June 28, 1966 M. GOTTFRIED Re. 26,046

PRESSURE BANDAGE-SPLINT

Original Filed Jan. 23, 1962

INVENTOR.
MAX GOTTFRIED

BY

ATTORNEYS

United States Patent Office

Re. 26,046
Reissued June 28, 1966

26,046
PRESSURE BANDAGE-SPLINT

Max Gottfried, Rossford, Ohio, assignor to Jobst Institute, Inc., Toledo, Ohio, a corporation of Ohio Original No. 3,153,413, dated Oct. 20, 1964, Ser. No. 177,693, Jan. 23, 1962. Application for reissue July 26, 1965, Ser. No. 479,685
8 Claims. (Cl. 128—87)

Matter enclosed in heavy brackets [ ] appears in the original patent but forms no part of this reissue specification; matter printed in italics indicates the additions made by reissue.

The invention relates to a new type of medical and surgical aid and more particularly to an improvement in pressure bandages. The invention can be embodied in manufacturers which are useful as improvements in old devices which are capable of providing pressure either static or pulsating. The invention can also be embodied in novel forms of medical and surgical devices having functions not heretofore attainable with any previously available product of manufacture.

The invention may be regarded as an improvement in pressure bandages, or splints, or pneumatic garments or other pressure devices. The invention may also be considered as a means for embodying a new concept in devices for medical and surgical aids. In this latter aspect, the invention has for one of its objects the provision of a bandage so constructed that the body contained within it may be visually inspected while it is immobilized.

Another object is to provide a device which may quickly and easily be applied to an injured part of the body and the device may then be easily manipulated to provide pressure.

A further object is to construct a pressure bandage in such form that it is capable of being used as a splint which not only adequately supports the injured member but also permits visual inspection of the insured member without removal of the support.

A further object is to provide a bandage which can readily be applied quickly in the vicinity where an accident occurs and will quickly and effectively function to stop or retard bleeding and swelling.

These and other objects are obtained by the novel pressure bandage of my invention as hereinafter more particularly described and illustrated wherein.

Figure 1:
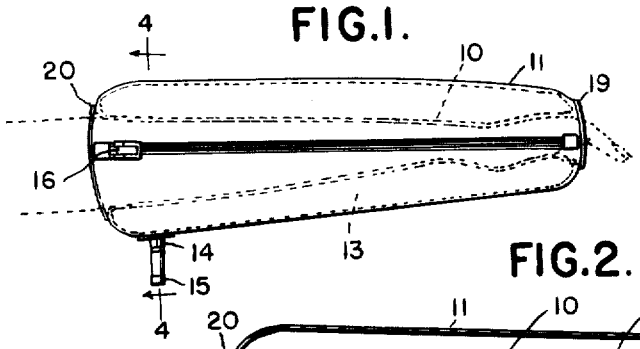
FIGURE 1 is an elevational view of the invention as applied to an injured arm.
Figure 2:
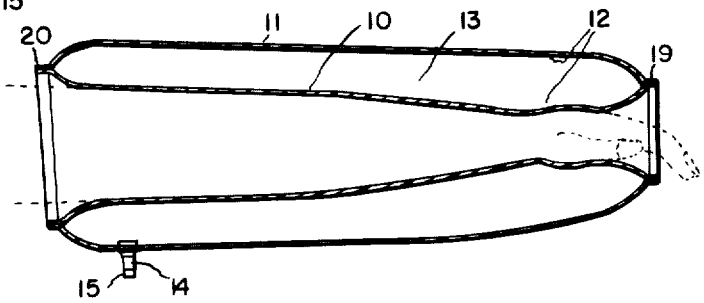
FIGURE 2 is a longitudinal section, somewhat enlarged, on line 2—2 of FIGURE 4.
Figure 3:
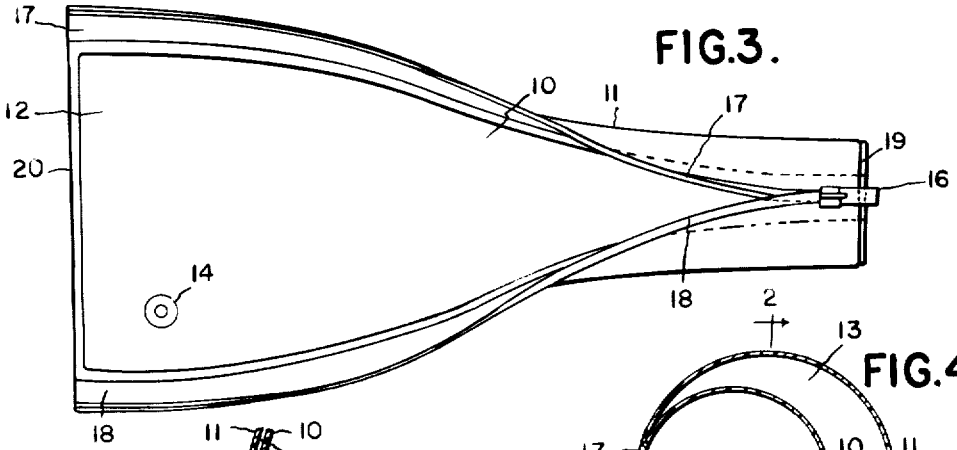
FIGURE 3 is a view of a deflated bandage partially open.

Referring to FIGURE 3, the pressure bandage of the invention consists of two flexible sheets of suitable material designated as inner sheet 10 and outer sheet 11. The two sheets have their margins joined to each other throughout the entire periphery thereby forming a two-ply assembly 12 with a chamber 13 between the respective sheets. The material must be sufficiently impervious to gases so that when the sheets are marginally hermetically sealed, the chamber can maintain a substantial pressure. A valve stem 14 is affixed to the outer sheet and provided with a manually operated valve 15 permitting inflation of the chamber and retention of the desired degree of pressure therein.

16 is a slide fastener connecting the opposite longitudinally extending margins 17 and 18 respectively of the two-ply assembly. By operating the slide fastener, the initially flat fabric can be bent into cylindrical form adapted to fit about the portion of the human body for which the bandage is designed. As illustrated, the bandage is represented in a suitable form to fit about a human arm.

Figure 4:
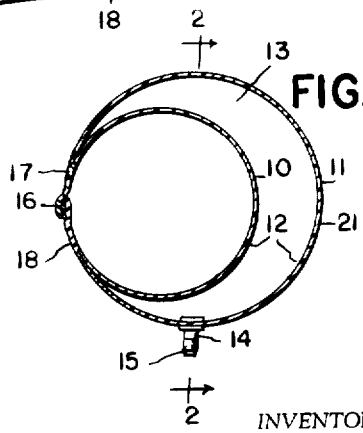
FIGURE 4 is an enlarged cross-section of the inflated bandage on line 4—4 of FIGURE 1.
Figure 5:
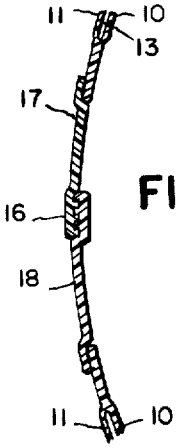
FIGURE 5 is an enlarged sectional view illustrating the slide fastener.

When the longitudinal edges are joined together by the slide, the laterally extending margins 19 and 20 become doubled upon themselves while the fabric is flat and the chamber deflated. Upon inflating the chamber through the valve, the lateral margins 19 and 20 are expanded into circular form and the outer enveloping sheet 11 is expanded into cylindrical form having a circular cross-section as illustrated at 21 in FIGURE 4. The inner sheet 10 is collapsed by the pressure of air within the chamber 13 and it assumes the form and configuration of whatever object is within the bandage. Because the outer and inner envelopes are joined at both longitudinal margins 17 and 18, the chamber 13 between these envelopes assumes a cross-sectional shape which is unsymmetrical with respect to the cross-section 21 of the outer envelope 11. The inner enveloping sheet 10 is collapsed by the pressure within the chamber 13 so that the fabric thereof comes in intimate contact with the outer configuration of the body within the same. As shown in FIGURE 4, the inner envelope 10 is pictured in circular form eccentric with respect to the outer circle 21. It should be understood however that this inner envelope is not necessarily truly circular but has the curvature of the contained body. Thus, the material of the inner envelope is not necessarily smooth but folds upon itself to the extent necessary to conform with the configuration of the contained object. If the bandage is inflated without any contained object, the inner enveloping sheet is completely collapsed.

In order to provide for visual inspection, the inner and outer envelopes are both made from a transparent fabric. The outer envelope must be composed of a material sufficiently nonelastic to prevent undue stretching under pressure. The inner envelope must be pliable so that it will conform to the shape of the body which it envelops. A suitable material for the outer sheet is twelve gauge polished polyvinyl chloride made by Union Carbide under its designated KDA 2940. A material for the inner sheet is eight gauge cast polyvinyl chloride made by Union Carbide under its designated VBA 9930. These materials are commercially obtainable. Equivalent polyvinyl chloride materials suitable for the outer and inner sheets are manufactured by Allied Chemical, Du Pont and Rohm & Haas. When using plastic materials, the margins of the sheets are preferably connected together by heat sealing in the manner well known in the art.

The valve and valve stem are commercial products. Opening and closing of the valve is accomplished by twisting the valve in the stem. Usually a hand operated bulb is provided for inflation, but any other inflating means may be used. In emergencies, the bandage may be inflated by mouth.

The invention herein described has many important advantages. In the case of a fractured arm or leg, the bandage may be applied with little movement of the limb. As soon as the slide fastener is closed, the bandage is immediately inflated and the limb is thereby provided with a splint for rendering it immobile. The injured person is therefore protected during transportation. A doctor can visually inspect the injured member without removing the device.

The device functions to control bleeding instantly and it controls formation of injuring edema. The pressure in the bandage may be raised or lowered as desired in accordance with the severity of the wound. The invention permits constant observation while the bandage is applied and provides a means for quick removal whenever necessary.

What I claim as my invention is:

1. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible, transparent plastic material of lesser thickness than said outer envelope, said inner envelope being substantially free from attachment to said outer envelope except at said sealed margins, and means for applying oral pressure to inflate said chamber between said sheets forming the latter, thereby expanding said outer envelope into circular cross section, while causing said inner envelope to move radially inward into continuous contact with the contained body member and in eccentric relation to said outer envelope, said connection for the longitudinal margins being in the form of a slide fastener having coacting members secured on said double-walled envelope along said longitudinal sealed margins of said chamber.

2. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible polyvinyl chloride plastic material of lesser thickness than said outer envelope, said inner envelope being substantially free from attachment to said outer envelope except at said sealed margins, means for applying oral pressure to inflate said chamber between said sheets forming the latter, thereby expanding said outer envelope into circular cross section, while causing said inner envelope to move radially inward into continuous contact with the contained body member and in eccentric relation to said outer envelope, said connection for the longitudinal margins being in the form of a slide fastener having coacting members secured on said double-walled envelope along said longitudinal sealed margins of said chamber, said inflating means including a valve stem secured to said outer envelope, a twist valve in said valve stem, said margins being secured together by a heat seal, and said outer envelope being polyvinyl chloride of a thickness to resist stretching under inflation pressure.

3. A pressure bandage-splint comprising a pair of initially flat sheets sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a transparent plastic material sufficiently non-elastic to of itself prevent its substantial stretching under oral inflation pressure, said inner envelope being composed of a transparent plastic material of lesser thickness than said outer envelope and sufficiently pliable so that under said inflation pressure the inner envelope will conform to the shape of the body member, said connection for the longitudinal margins being in the form of a slide fastener having coacting members secured on said double-walled envelope along said longitudinal margins, and means for applying oral pressure to inflate said chamber between said sheets forming the latter, thereby expanding the outer envelope into circular cross section while causing said inner envelope to move radially inward into continuous pressure contact with the contained body member, said inflating means including a valve stem secured to said outer envelope and a twist valve in said valve stem, said outer envelope being polyvinyl chloride of thickness not less than twelve gauge and said inner envelope being polyvinyl chloride of thickness not greater than eight gauge.

*4. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible, transparent plastic material said inner envelope being substantially free from attachment to said outer envelope except at said sealed margins, and means for applying oral pressure to inflate said chamber between said sheets forming the latter, thereby expanding said outer envelope into circular cross section, while causing said inner envelope to move radially inward into continuous contact with the contained body member, said connection for the longitudinal margins being in the form of a slide fastener having coacting members secured on said double-walled envelope along said longitudinal sealed margins of said chamber.*

*5. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible, transparent plastic material, said inner envelope being substantially free from attachment to said outer envelope except at said sealed margins, and means for applying oral pressure to inflate said chamber between said sheets forming the latter, thereby expanding said outer envelope into circular cross section, while causing said inner envelope to move radially inward into continuous contact with the contained body member, and in eccentric relation to said outer envelope, said connection for the longitudinal margins being in the form of a slide fastener having coacting members secured on said double-walled envelope along said longitudinal sealed margins of said chamber.*

*6. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible polyvinyl chloride plastic material, said inner envelope being substantially free from attachment to said outer envelope except at said sealed margins, means for applying oral pressure to inflate said chamber between said sheets forming the latter, thereby expanding said outer envelope into circular cross section, while causing said inner envelope to move radially inward into continuous contact with the contained body member, said connection for the longitudinal margins being in the form of a slide fastener having coacting members secured on said double-walled envelope along said longitudinal sealed margins of said chamber, said inflating means including a valve stem secured*

*to said outer envelope, a twist valve in said valve stem, said margins being secured together by a heat seal, and said outer envelope being polyvinyl chloride of a thickness to resist stretching under inflation pressure.*

*7. A pressure bandage-splint comprising a pair of initially flat sheets hermetically sealed at the longitudinal and lateral margins forming therebetween an inflatable chamber, the longitudinal margins being connected together to form a double-walled envelope for surrounding a body member with said sheets constituting inner and outer envelopes, said outer envelope being composed of a flexible, collapsible, transparent plastic material sufficiently non-elastic to of itself prevent its substantial stretching under oral inflation pressure, said inner envelope being composed of a pliable, flexible, collapsible, transparent plastic material, and means for applying oral pressure to inflate said chamber between said sheets forming the latter, thereby expanding said outer envelope into circular cross section, while causing said inner envelope to move radially inward into continuous contact with the contained body member, said connection for the longitudinal margins being in the form of a slide fastener having coacting members secured on said double-walled envelope along said longitudinal sealed margins of said chamber, said inner envelope being sufficiently free from attachment to said outer envelope intermediate the longitudinal margins thereof to insure that said inflatable chamber affords a space which extends from said connected longitudinal margins continuously and uninterruptedly in*

*opposite circular directions for a substantial portion of the total circular perimeter of said outer envelope.*

*8. A pressure bandage-splint according to claim 7 in which said connected longitudinal margins are in edge to edge relation with each other without substantial overlap, and the seals at said longitudinal margins are of narrow width so that said space within said inflatable chamber is closely adjacent the line of said edge to edge relation.*

References Cited by the Examiner

The following references, cited by the Examiner, are of record in the patented file of this patent or the original patent.

UNITED STATES PATENTS

| | | | |
|---|---|---|---|
| 2,267,070 | 12/1941 | Baldwin | 128—165 |
| 2,272,481 | 2/1942 | Rinkes et al. | 128—165 |
| 2,582,648 | 1/1952 | Mowbray | 128—165 |
| 2,651,302 | 9/1953 | Berry | 128—87 |
| 2,694,395 | 11/1954 | Brown | 128—165 |
| 2,832,336 | 4/1958 | Davis et al. | 128—38 |
| 2,834,340 | 5/1958 | Walter | 128—84 |

FOREIGN PATENTS

| | | |
|---|---|---|
| 549,294 | 11/1942 | Great Britain. |

RICHARD A. GAUDET, *Primary Examiner.*

L. W. TRAPP, *Assistant Examiner.*